(12) United States Patent
Pellachin

(10) Patent No.: US 8,793,888 B2
(45) Date of Patent: Aug. 5, 2014

(54) DEVICE FOR MEASURING THE ANGLES OF INCLINATION OF THE INCISOR OCCLUSAL PLANE OF EQUIDAE AND OTHER ANIMALS

(76) Inventor: Matteo Pellachin, Padua (IT)

( * ) Notice: Subject to any disclaimer, the term of this patent is extended or adjusted under 35 U.S.C. 154(b) by 292 days.

(21) Appl. No.: 13/514,127

(22) PCT Filed: Dec. 10, 2009

(86) PCT No.: PCT/IB2009/055648
§ 371 (c)(1),
(2), (4) Date: Jun. 6, 2012

(87) PCT Pub. No.: WO2011/070396
PCT Pub. Date: Jun. 16, 2011

(65) Prior Publication Data
US 2012/0246954 A1    Oct. 4, 2012

(51) Int. Cl.
*A61C 19/045*    (2006.01)
*A61B 5/107*    (2006.01)
*A61B 5/00*    (2006.01)
*A61D 5/00*    (2006.01)

(52) U.S. Cl.
CPC ............... *A61B 5/4547* (2013.01); *A61D 5/00* (2013.01); *A61C 19/045* (2013.01); *A61B 5/1071* (2013.01); *A61B 2503/40* (2013.01)
USPC ............................................. 33/511; 433/68

(58) Field of Classification Search
CPC ...... A61C 19/045; A61C 19/05; A61B 5/103; A61B 5/107; A61B 5/1071
USPC .................................. 33/511; 433/73, 69, 68
See application file for complete search history.

(56) References Cited

U.S. PATENT DOCUMENTS

| | | | |
|---|---|---|---|
| 1,052,806 A * | 2/1913 | Evans ........................... | 433/73 |
| 3,336,670 A | 8/1967 | Heydenreich | |
| 3,382,581 A * | 5/1968 | Laszlo Balazs ................ | 433/27 |
| 4,096,637 A * | 6/1978 | Stade .............................. | 33/514 |
| 4,443,191 A | 4/1984 | Gutierrez | |
| 4,872,268 A * | 10/1989 | Perrault ......................... | 33/512 |
| 5,078,600 A | 1/1992 | Austin | |
| 5,176,515 A * | 1/1993 | Andrews ........................ | 433/24 |
| 6,109,917 A * | 8/2000 | Lee et al. ....................... | 433/73 |
| 6,582,931 B1* | 6/2003 | Kois et al. ...................... | 435/56 |
| 7,048,539 B2* | 5/2006 | Mack .............................. | 433/73 |
| 7,699,607 B2* | 4/2010 | Margossian .................... | 433/73 |
| 2006/0003285 A1* | 1/2006 | Kotsuchibashi et al. ....... | 433/68 |
| 2008/0057466 A1 | 3/2008 | Jordan et al. | |
| 2012/0244490 A1* | 9/2012 | Tamburrino et al. ........... | 433/73 |

* cited by examiner

*Primary Examiner* — Christopher Fulton
(74) *Attorney, Agent, or Firm* — Themis Law

(57) ABSTRACT

A device for measuring anatomical dimensions of animals, and particularly the angle of inclination between the occlusal plane of an animal, defined by the contact surface between its upper and lower dental arches, and the alternative reference planes passing either through the anterior sagittal point and the temporomandibular joints, or through the anterior sagittal point and the eyes of the animal includes an element of contact with the animal, at least one first movable member attached revolvingly to the contact element around a first axis of rotation, and at least one graduated scale situated on the contact element, or on the first movable element to enable the measurement of their relative rotation. The contact element also includes a locator plate sized to fit inside the animal's mouth between its upper and lower dental arches, and to be aligned with the occlusal plane.

14 Claims, 5 Drawing Sheets

DEVICE FOR MEASURING THE ANGLES OF INCLINATION OF THE INCISOR OCCLUSAL PLANE OF EQUIDAE AND OTHER ANIMALS

FIELD OF THE INVENTION

The present invention is generally applicable to the animal breeding sector and particularly concerns a device for measuring anatomical dimensions of animals of the type described herein.

BACKGROUND OF THE INVENTION

There are numerous known devices for measuring the dimensions or angular asymmetries of persons or animals.

In particular, WO9908064 describes a device for measuring the width of the mouth of a horse or other animal. The device comprises an elongated crossbar with a graduated scale extending along its length and two contact elements designed to abut against two opposite sides of the animal's mouth. At least one of the two contact elements is movable along the elongated crossbar to obtain the measurement, while the other can be positioned proximal to one longitudinal end. The measurement is obtained by inserting the elongated crossbar inside the animal's mouth and subsequently positioning the two contact elements in line with the left and right sides of the animal's mouth. The measurement of the width can thus be read on the graduated scale.

U.S. Pat. No. 6,178,652 describes a device for measuring a horse's head comprising a plurality of belts designed to be positioned on the horse's head using adjustable closing means. The shape of the belts substantially resembles that of the bridles commonly used for horses. The belts are marked with numbered scales along their length and include suitable reading windows that enable a reading of the lengths associated with the belts. Thus, after adjusting the closing means to make the belts adhere to the horse's head, the measurements of numerous physical lengths of interest can be viewed through the reading windows.

One evident disadvantage of the above-described solutions lies in that neither of the two devices allow for the measurement of any angular misalignments between certain anatomical points of interest, e.g. between the teeth and the temporomandibular joint or the eyes of the animal. The solutions described are restricted to the measurement of lengths, from which it is difficult or impossible to derive an indirect measurement of any angular misalignments with an acceptable degree of uncertainty.

U.S. Pat. No. 5,678,317 describes a device for measuring the angular asymmetries of the human face. The device comprises two shanks hinged to one another so that they can be rotated relative to one another. On one of the two shanks there is a graduated scale that enables the angle coming between the two shanks to be measured. One shank is juxtaposed to the face and aligned with one direction of symmetry on the face, while the other shank is rotated until it comes into line with the physical feature of which we wish to measure the angle of inclination in relation to the selected direction of symmetry. The measurement is obtained by reading the angle on the graduated scale.

One disadvantage of this solution lies in that it is only possible with ease to measure one angle between two directions, but not the dual angular inclination of one plane of interest in relation to a second plane of reference. In the field of animals in particular, as concerns mastication, there are two planes of reference that can be considered, i.e. a plane passing through the anterior sagittal point and the temporomandibular joints, and a plane passing through the anterior sagittal point and the eyes.

The drawback of the above-mentioned instrument is consequently particularly evident in the field of equine species, because it does not enable a measurement of the dual latero-lateral inclination, relating to the incisor plane with respect to the axis of the eyes or to the axis passing through the temporomandibular joints, in combination with the antero-posterior inclination of the horse's incisor occlusal plane in relation to said corresponding axes of reference passing through the temporomandibular joints and/or the eyes. The ability to measure not the antero-posterior angle of the real incisor occlusal plane in the anterior sagittal point, but only the two angles lateral thereto, will give rise—in the event of a latero-lateral inclination of the incisor plane—to different antero-posterior measurements depending on whether they are obtained on the right or left side of the head. The combined measurement may be useful to obtain fundamental information on the animal's present and future state of health inasmuch as an incorrect inclination of the incisor occlusal plane can severely restrict jaw movement, causing the animal recurrent discomfort.

Another disadvantage of the above-mentioned instrument lies in that simply holding the device up against the animal and keeping it in position while taking the measurement may not be easy, particularly if the animal moves.

SUMMARY OF THE INVENTION

A primary object of the present invention is to overcome the above-described drawbacks by means of a measuring device that enables the dual inclination of a plane of interest to be measured with respect to a reference plane.

A particular object of the invention is to provide a device that is easy and practical to use to obtain measurements on animals, and on horses in particular.

Another object of the invention is to provide a device that enables a measurement to be obtained with a high degree of accuracy and a relatively limited uncertainty.

An additional object of the invention is to provide a device that is minimally invasive and uncomfortable for the animal being measured.

These objects, as well as others that will become apparent later on, are achieved, by a device for measuring anatomical dimensions of animals, and particularly the angle of inclination between the incisor occlusal plane (defined by the contact surface between the upper and lower incisor dental arches of an animal) and the incisor occlusion reference planes, i.e. the reference plane passing through the anterior sagittal point B of the occlusal plane, which, as shown in FIG. 4, is defined by the intersection of the sagittal plane PS with the real incisor occlusal plane PO and with a limit anterior plane PR perpendicular to both the sagittal plane PS and the real incisor occlusal plane PO and passing through the most anterior point of the upper or lower dental arch, and the reference plane passing through the anterior sagittal point B and the animal's eyes.

The device comprises an element of contact with the animal, at least one first movable member revolvingly connected to the contact element around a first axis of rotation, and at least one graduated scale, located on the contact element or on the first movable member, for measuring their relative rotation. This is the latero-lateral angular measurement, illustrated in FIG. 7. In addition, the contact element comprises a locator plate sized to fit inside the animal's mouth, between the upper and lower dental arches, and to be aligned with the masticatory plane. The first axis of rotation is given by the anterior extension of the straight intersecting line between the locator plate and the sagittal plane. An integral abutment is attached orthogonally and transversely to one side of the locator plate, against which the teeth of the animal's upper or lower dental arches make contact, depending on how the instrument is inserted. A point is defined where a first intersecting line coming between the locator plate and the sagittal plane crosses over a second, crosswise intersecting line between the locator plate and the abutment. The axis of rotation parallel to the first movable member, and integral therewith, extends from this point. The antero-posterior angle of the incisor plane with respect to the temporomandibular joint and to the ipsilateral eye is measured from this transversal axis on a plane parallel to the sagittal plane.

The first movable member comprises a second graduated scale in a position orthogonal to the first. This second scale is accompanied by a second movable member on the previously-described antero-posterior axis of rotation. This second movable member must be aligned with the temporomandibular joint or the ipsilateral eye to enable a measurement on the second scale of the angle of inclination of the second movable member in relation to the locator plate.

This particular configuration makes it possible to obtain a measuring device that is particularly practical to use for measuring animals, and horses in particular, and that is capable of ensuring a high level of precision, referring the measurements of the latero-lateral and antero-posterior angles of inclination to the only line on the sagittal plane of the head that intersects the incisor occlusal plane.

BRIEF DESCRIPTION OF THE DRAWINGS

The characteristics of the new measuring device will be better clarified in the description that follows with reference to the attached drawings illustrating a non-limiting example.

DETAILED DESCRIPTION OF A PREFERRED EMBODIMENT OF THE INVENTION

Figure 1:
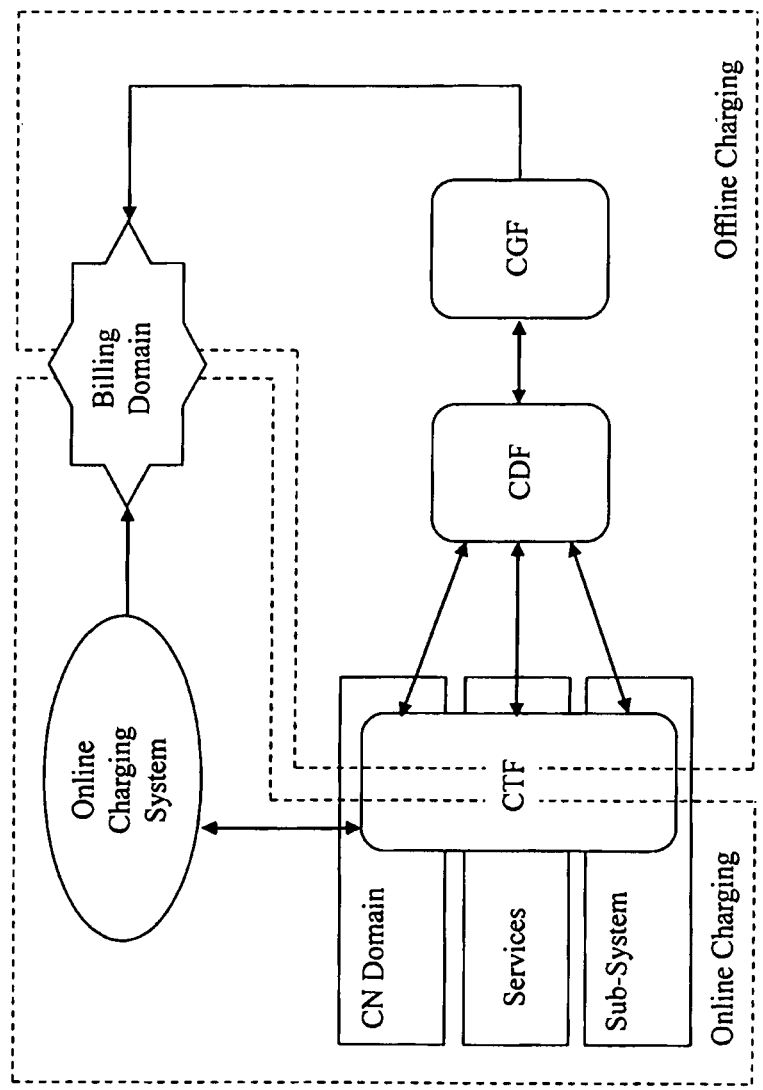
FIG. 1 shows a front view of a device according to the invention with a schematic representation of the animal's head.
Figure 2:
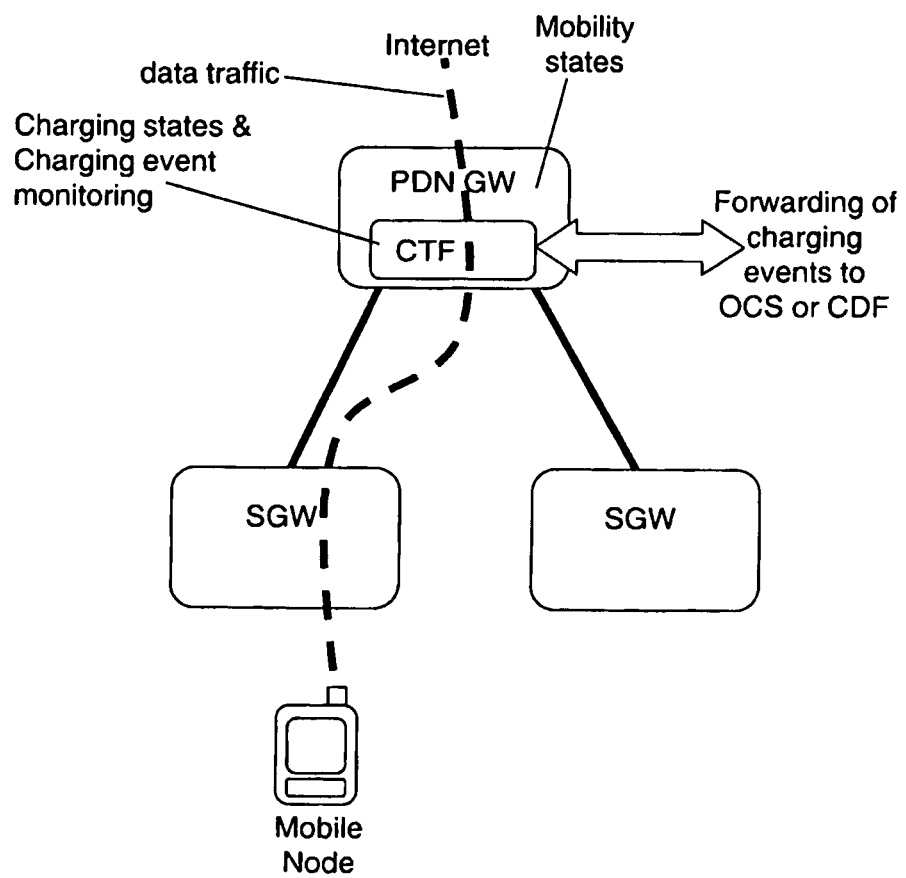
FIG. 2 shows a side view of a device according to the invention with a schematic representation of the animal's head.

An embodiment of a device according to the invention is described herein with particular reference to the attached figures. The reference numbers used in the description and claims are intended to facilitate the reader's understanding of the invention and shall not be construed as factors limiting the scope of the invention protected by the patent in any way.

The device for measuring anatomical dimensions of animals according to the invention, indicated globally by the reference number 1, is particularly suitable for measuring the angle of inclination between an incisor occlusal plane (not shown in the drawings) defined by the contact surface between the upper S and lower I incisor dental arches of an animal, and a reference plane (not shown in the drawings) passing through the midline of the incisor plane B and the temporomandibular joints T or, equally, a plane passing through the midline of the incisor plane B and the animal's eyes O. The device 1 comprises an element of contact with the animal 2, at least one first movable member 3 revolvingly connected to the contact element 2 around a first axis of rotation L1. There is at least one graduated scale 4, provided on the contact element 2 or on the first movable member 3, designed to enable the measurement of their relative rotation. A particular characteristic of the invention lies in that the contact element 2 comprises a locator plate 5 sized to fit inside the animal's mouth, between the upper S and lower I incisor dental arches, and to be aligned with the incisor occlusal plane; on one side of the locator plate there is an abutment PF against which the corresponding teeth of the animal's dental arch abut.

Figure 6:
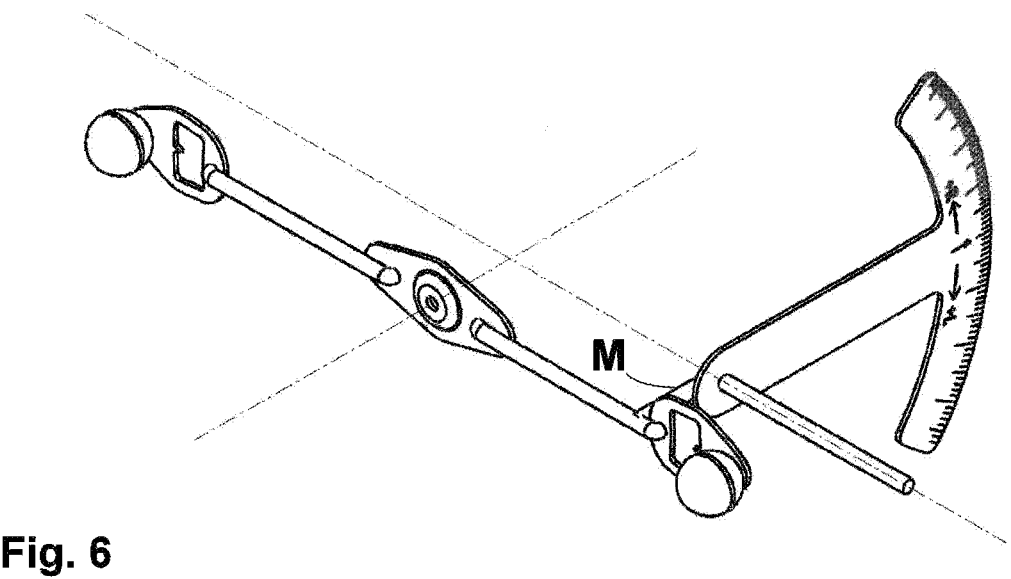
FIG. 6 shows the first movable member and its axes L1 and L2 that intersect the anterior sagittal point B and the support M.
Figure 7:
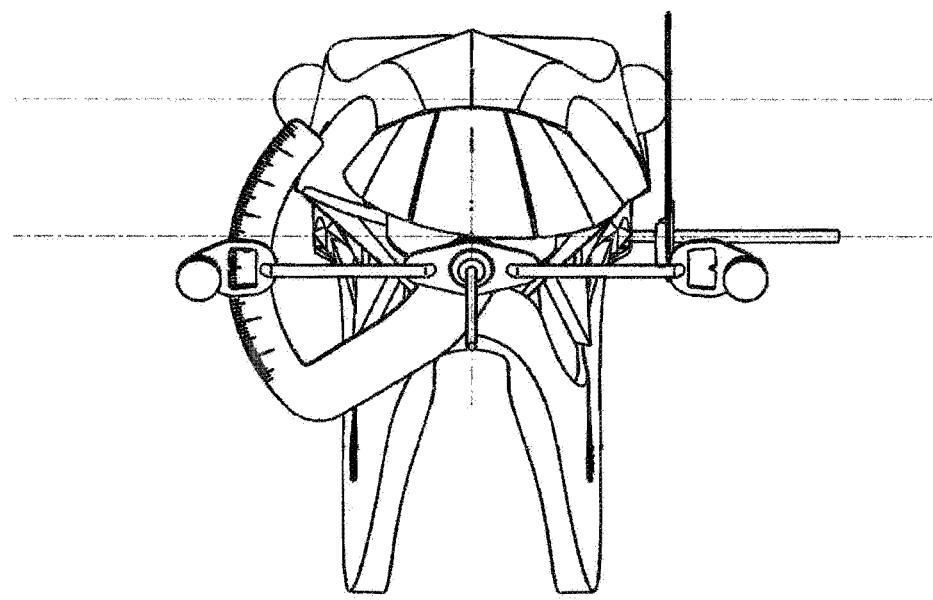
FIG. 7 shows the device on an occlusal plane with a latero-lateral inclination associated with an antero-posterior inclination.

The device 1 may include a second movable member 6, revolvingly connected to the first movable member 3 around a second axis of rotation L2. In particular, the first and second axes of rotation L1, L2 may be substantially orthogonal to each other (FIG. 6). This particular feature makes it possible to align both the first movable member 3 and the second movable member 6 with the reference plane. The locator plate 5 integral with the contact element 2 can thus be aligned with the animal's incisor occlusal plane, while the first and second movable members 3, 6 can be aligned with the reference plane. In these alignment conditions, the angle of inclination forming the object of the measurement between the occlusal plane and the reference plane can be identified from the two relative rotations between the contact element 2 and the first movable member 3, and between the latter and the second movable member 6.

In detail, when the locator plate 5 is aligned with the occlusal plane, the first axis of rotation L1 will always be aligned with the locator plate 5 and with the (longitudinal vertical) sagittal plane (not shown in the drawings) passing through the anterior sagittal point B and the midpoint between the animal's eyes O.

Figure 3:
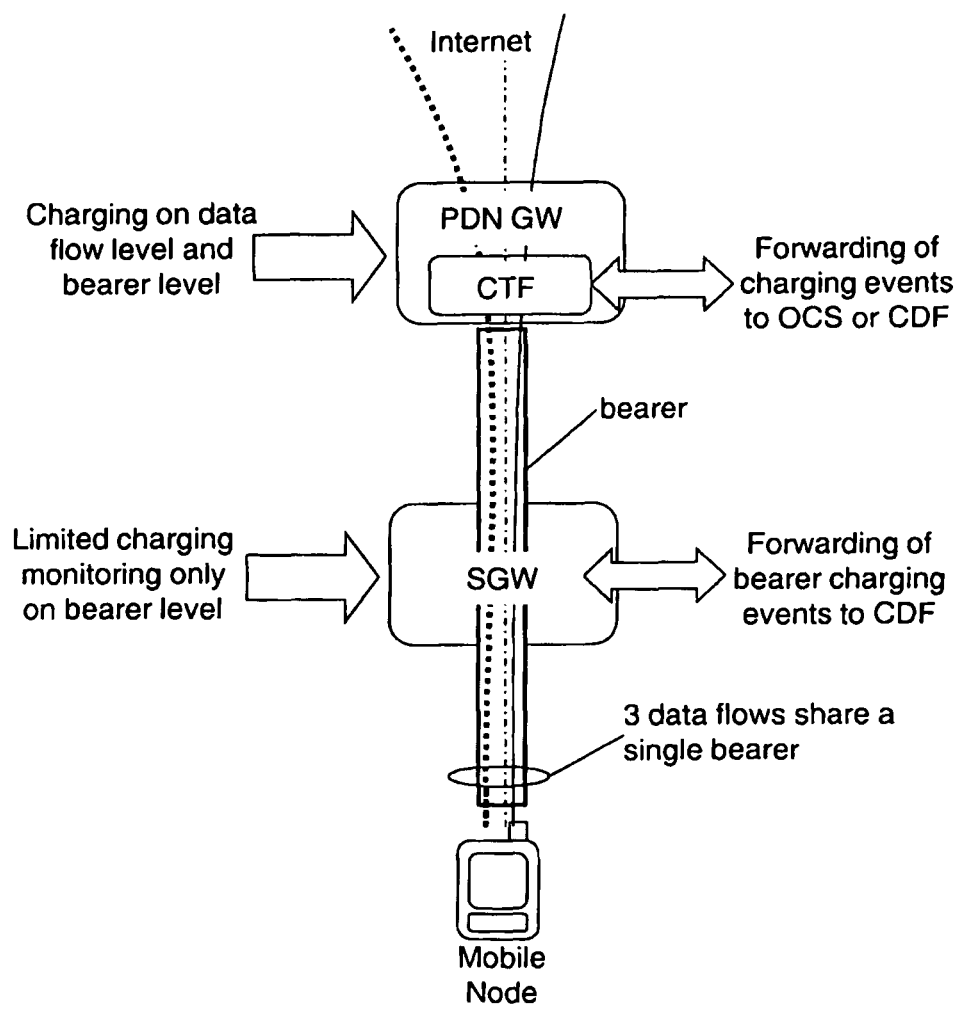
FIG. 3 shows a three-quarter view of a device according to the invention with a schematic representation of the animal's head.
Figure 4:
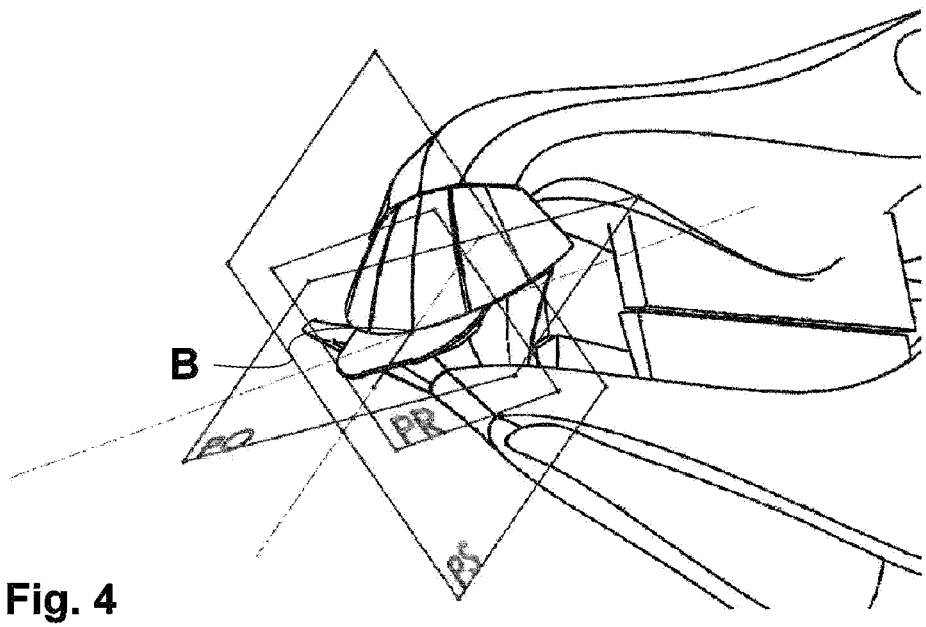
FIG. 4 shows the sagittal plane PS, the real occlusal plane PO, the limit anterior plane PR, the anterior sagittal point B, and the two axes of rotation L1 and L2.
Figure 5:
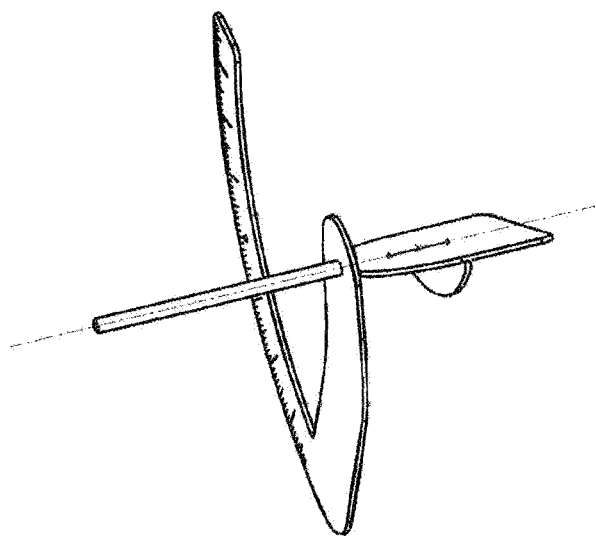
FIG. 5 shows the contact element in the configuration with the scale integral therewith.

As shown in FIGS. 1, 3, and 6, the first movable member 3 can comprise a crossbar 7, substantially orthogonal to the first axis of rotation L1, and two spherical elements, or alignment knobs 8, positioned at the ends of the crossbar 7. The angular stroke of the crossbar 7 with respect to the contact element 2 can be selected so that it is sufficient to achieve the alignment of the crossbar 7 with the reference plane and consequently with the animal's temporomandibular joints T or eyes O. The two knobs 8 can be used to facilitate the alignment of the crossbar 7 with the temporomandibular joints T or with the eyes O of the animal. The crossbar 7 can also be positioned substantially with its midpoint on the first axis of rotation L1, so that there are two lateral portions 9 of substantially the same length on either side of the center of rotation, defined by the intersection of the first axis of rotation L1 with the crossbar 7.

The graduated scale 4 can be positioned on the contact element 2, and integrally attached thereto, and the first movable member 3 can have a reading window 101 on the graduated scale 4 on the contact element 2. The reading window 101 can be positioned in the vicinity of one end of the crossbar 7, and the graduated scale 4 can be shaped so as to form an arc of a circle. The zero on the graduated scale 4 can be coplanar with the locator plate 5, so that the measurement obtained in the reading window 101 is nil when the crossbar 7 is substantially aligned with the locator plate 5, and consequently with the plane of occlusion. There is a second reading window 102 located at the other end of the crossbar 7, a mirror image of the first in relation to the axis L1. This second window serves the same purpose as the first, i.e. rotating the first movable element through 180° on the axis L1 enables the section designed to measure the antero-posterior angle (described in more detail below) to be displaced to the opposite side of the head, with the resulting advantage of enabling the second measurement of the antero-posterior angle to be compared with the first, thereby also identifying any asymmetries between the reference planes.

The first movable member 3 can include a support M for the device for measuring the antero-posterior angle in an orthogonal position near one of the two windows 101, 102 aligned in a direction parallel to the axis of rotation L1. This support M may be accompanied by a second movable member 6 on a perpendicular and integrally attached revolvable pin L2. The axis of the pin L2 is perpendicular to the first axis of rotation L1 and passes through the reference point where a first intersecting line between the locator plate 5 and the sagittal plane and a second crosswise intersecting line between the locator plate 5 and the abutment PF cross over, considered as the midline of the anterior sagittal point B.

The second movable member 6 may comprise a longitudinal bar 11 substantially orthogonal to the second axis of rotation L2.

The longitudinal bar 11 may be positioned substantially with one of its ends on the second axis of rotation L2. Thus, when the locator plate 5 is correctly positioned on the animal's occlusal plane and the crossbar 7 is aligned with the temporomandibular joints T or eyes O of the animal, the longitudinal bar 11 can rotate around a plane substantially orthogonal to the reference plane, and consequently parallel to the head's sagittal plane. As a result, the suitable rotation of the second movable member 6 around the axis of rotation L2 makes the longitudinal bar 11 become aligned with the direction defined by the line running from the anterior sagittal point B to the temporomandibular joints T, or from the anterior sagittal point B to the eyes O, thereby obtaining the alignment of said line with the reference plane passing through the anterior sagittal point B and the temporomandibular joints T, or with the reference plane passing through the midline of the animal's anterior sagittal point B and the animal's eyes O.

The longitudinal bar 11 may have a folding portion 12 distal to the second axis of rotation L2, designed to enable a partial adaptation to the shape of the animal's head and to facilitate the alignment of the longitudinal bar 11 with the animal's temporomandibular joints T or eyes O. The plane in which the bar 12 rotates is the same as that of the axis L2.

As shown in FIG. 3, the first movable member 3 may include a second graduated scale 13, integrally attached to the support M and similar to the graduated scale 4, for measuring the relative rotation between the first movable member 3 and the second 6. The second movable member 6 may have a reading window 14 on the second graduated scale 13. The reading window 14 and the second graduated scale 13 enable the second angle of interest to be measured when both the crossbar 7 and the longitudinal bar 11 are aligned with the reference plane anterior sagittal point B—temporomandibular joints or anterior sagittal point B—eyes.

From the above description, it is evident that the device according to the invention achieves the previously-stated objects and, in particular, it enables the easy and accurate measurement of the two angles that define the position of the occlusal plane of an animal in relation to a reference plane passing through the anterior sagittal point B and the animal's temporomandibular joints or, equally, through the anterior sagittal point B and the animal's eyes.

Thus, with reference to the previous description and to the attached drawings, the following claims are advanced.

The invention claimed is:

1. A device suitable for measuring an angle of inclination between actual and reference incisor occlusal planes in an animal comprising:
    a contact element having a first rotation axis coinciding with an intersection line between a sagittal plane and an actual incisor occlusal plane;
    a first movable member rotatably coupled to said contact element around said first rotation axis;
    a graduated scale provided on said contact element or on said first movable member for measuring a relative rotation thereof, wherein said contact element comprises a locator plate sized to fit inside an animal's mouth between the upper and lower dental arches, and to be aligned with said incisor occlusal plane;
    an abutment plane coupled to said locator plate and aligned with a limit anterior plane perpendicular to said sagittal plane and said actual incisor occlusal plane, such to define an anterior sagittal point by an intersection of said limit anterior plane with said sagittal plane and with said actual occlusal plane; and
    a second movable member rotatable about a second rotation axis which is perpendicular to and which meets said first rotation axis in said anterior sagittal point, said second movable member being rotatably coupled to said contact element.

2. The device according to claim 1, wherein, after said first movable member has been aligned on a horizontal plane regardless of actual position of said actual incisor occlusal plane, said device is configured to position said second rotation axis orthogonally to said sagittal plane on said anterior sagittal point, independently of whether said second movable member is positioned on one side or another of said sagittal plane.

3. The device according to claim 1, further comprising a second graduated scale coupled to said first or said second movable member for measuring a relative rotation between said first and said second movable members.

4. The device according to claim 3, wherein, after said first movable member has been aligned on a horizontal plane, rotation of said second movable member occurs on a plane parallel to said sagittal plane for its alignment with temporomandibular joints of said animal, and wherein the said second graduated scale is disposed on a plane parallel to said sagittal plane such to provide a reading of an inclination of said actual incisor occlusal plane with respect to a reference incisor occlusal plane.

5. The device according to claim 3, wherein said first movable member comprises a crossbar substantially orthogonal to said first rotation axis and parallel to said second rotation axis, an angular stroke of said crossbar in relation to said contact element allowing an alignment of said crossbar with a reference plane containing said anterior sagittal point and an axis connecting eyes of said animal or or temporomandibular joints of said animal.

6. The device according to claim 5, wherein said first movable member comprises two spherical alignment elements positioned at ends of said crossbar such to facilitate grip for said alignment of said crossbar.

7. The device according to claim 5, further comprising a reading window of said graduated scale located on said contact element, said reading window being positioned in proximity to at least one end of said crossbar.

8. The device according to claim 5, wherein said second movable member comprises a longitudinal rod substantially orthogonal to said second rotation axis, an angular stroke of said longitudinal rod in relation to said first movable member allowing said longitudinal rod to be aligned with said reference plane.

9. The device according to claim 8, wherein said second graduated scale comprises a zero index, positioned on a plane determined by said first and said second rotation axes, and right/left or positive/negative indices to measure rotation of said longitudinal rod in relation to a plane containing said first and said second rotation axes.

10. The device according to claim 8, wherein a correct alignment of said crossbar with said temporomandibular joints is confirmed when a reading of said second graduated scale with said longitudinal rod aligned with a same side temporomandibular joint after a 180° rotation of said first movable member (3), is equal to a reading of said second graduated scale positioned on an opposite side of said animal.

11. The device according to claim 8, wherein said longitudinal rod has a folding portion configured to be moved on a same plane as said second rotation axis, said folding portion being positioned on an opposite end of said longitudinal rod than said second rotation axis.

12. The device according to claim 5, further comprising a third reading window positioned at an end of said crossbar and configured read rotation of said first movable member by precisely 180°, thereby providing a reading of an anterior-posterior inclination angle and confirming correct alignment in relation to a horizontal plane of said first movable member if readings of said first and third reading windows are identical or, if said readings are different, identifying inclination thereabout.

13. The device according to claim 3, wherein said second movable member comprises a reading window of said second graduated scale for reading a measure of a relative rotation between said first and second movable members.

14. The device according to claim 1, wherein said incisor occlusal plane is configured to measure position of dental arches or parts thereof of an equine animal.

* * * * *